US010980422B2

(12) United States Patent
Schneider et al.

(10) Patent No.: US 10,980,422 B2
(45) Date of Patent: Apr. 20, 2021

(54) METHOD FOR VISUALIZING A TOOTH SITUATION

(71) Applicant: DENTSPLY SIRONA inc., York, PA (US)

(72) Inventors: Sascha Schneider, Muhltal (DE); Evgenij Derzapf, Lorsch (DE); Ravid Aloni, Gross-Rohrheim (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/775,601

(22) PCT Filed: Nov. 17, 2016

(86) PCT No.: PCT/EP2016/077934
§ 371 (c)(1),
(2) Date: May 11, 2018

(87) PCT Pub. No.: WO2017/085160
PCT Pub. Date: May 26, 2017

(65) Prior Publication Data
US 2018/0249912 A1    Sep. 6, 2018

(30) Foreign Application Priority Data
Nov. 18, 2015    (DE) ................... 10 2015 222 782.0

(51) Int. Cl.
*A61B 5/00*    (2006.01)
*A61B 1/24*    (2006.01)
(Continued)

(52) U.S. Cl.
CPC .............. *A61B 5/0077* (2013.01); *A61B 1/24* (2013.01); *A61B 5/0088* (2013.01);
(Continued)

(58) Field of Classification Search
CPC ................ A61B 1/24; A61B 2034/102; A61B 2034/105; A61B 2034/107;
(Continued)

(56) References Cited

U.S. PATENT DOCUMENTS

2004/0029068 A1*    2/2004    Sachdeva ................ A61C 7/00
433/24
2007/0217683 A1*    9/2007    Kinoshita .......... G06K 9/00214
382/190

(Continued)

FOREIGN PATENT DOCUMENTS

DE    202008014344 U1    3/2010
DE    102012110491 A1    5/2014
(Continued)

OTHER PUBLICATIONS

International Preliminary Report on Patentability (IPRP) Chapter I; PCT/EP2016/077934; Mar. 9, 2017 (completed); dated Mar. 21, 2017.
(Continued)

*Primary Examiner* — Michael J Vanchy, Jr.
(74) *Attorney, Agent, or Firm* — Dentsply Sirona Inc.

(57) ABSTRACT

Method for visualizing a tooth situation. The invention relates to a method for visualizing a tooth situation, wherein an image of the face of a patient is recorded and stored as a facial data record (1), feature points (3) within the facial data record (1) are automatically recognized by means of a facial recognition method, a mouth area (4) located between the lips is recognized automatically on the basis of the feature points (3), a position of the face in the facial data record (1) and a three-dimensional direction (5) of an orientation of the face in the facial data record (1) is automatically recognized on the basis of the feature points (3), a virtual tooth data record (2) of the tooth situation is oriented according to the three-dimensional direction (5) of the orientation of the face
(Continued)

and is positioned according to the position of the face with respect to the facial data record (1), the mouth area within the facial data record (1) is partially overlaid and/or overlaid and/or replaced by the tooth data record (2), and the result is displayed as a visualization data record.

12 Claims, 3 Drawing Sheets

(51) Int. Cl.
| | | |
|---|---|---|
| *A61B 5/1171* | (2016.01) | |
| *A61C 9/00* | (2006.01) | |
| *A61C 13/00* | (2006.01) | |
| *G16H 10/60* | (2018.01) | |
| *G16H 30/20* | (2018.01) | |
| *G16H 50/50* | (2018.01) | |
| *A61B 34/20* | (2016.01) | |
| *A61B 90/00* | (2016.01) | |
| *A61B 34/10* | (2016.01) | |
| *G06K 9/00* | (2006.01) | |
| *G06F 3/01* | (2006.01) | |
| *G16H 30/40* | (2018.01) | |
| *G06T 11/60* | (2006.01) | |

(52) U.S. Cl.
CPC .......... *A61B 5/1176* (2013.01); *A61B 5/4547* (2013.01); *A61B 5/7425* (2013.01); *A61B 34/10* (2016.02); *A61B 34/20* (2016.02); *A61B 90/36* (2016.02); *A61C 9/0053* (2013.01); *A61C 13/0004* (2013.01); *G06F 3/012* (2013.01); *G06K 9/00248* (2013.01); *G06K 9/00281* (2013.01); *G16H 10/60* (2018.01); *G16H 30/20* (2018.01); *G16H 30/40* (2018.01); *G16H 50/50* (2018.01); *A61B 2034/102* (2016.02); *A61B 2034/105* (2016.02); *A61B 2034/107* (2016.02); *A61B 2034/2065* (2016.02); *A61B 2034/2074* (2016.02); *A61B 2090/365* (2016.02); *A61B 2090/368* (2016.02); *A61B 2576/02* (2013.01); *G06T 11/60* (2013.01); *G06T 2210/41* (2013.01); *G09G 2340/12* (2013.01)

(58) Field of Classification Search
CPC .... A61B 2034/2065; A61B 2034/2074; A61B 2090/365; A61B 2090/368; A61B 2576/02; A61B 34/10; A61B 34/20; A61B 5/0077; A61B 5/0088; A61B 5/1176; A61B 5/4547; A61B 5/7425; A61B 90/36; A61C 13/0004; A61C 9/0053; G06F 3/012; G06K 9/00248; G06K 9/00281; G06T 11/60; G06T 2210/41; G09G 2340/12; G16H 10/60; G16H 30/20; G16H 30/40; G16H 50/50
See application file for complete search history.

(56) References Cited

U.S. PATENT DOCUMENTS

| | | | |
|---|---|---|---|
| 2009/0251557 A1* | 10/2009 | Kim | H04N 5/23219 348/222.1 |
| 2010/0145898 A1* | 6/2010 | Malfliet | G06T 7/0012 706/47 |
| 2012/0030578 A1 | 2/2012 | Athsani et al. | |
| 2012/0095732 A1 | 4/2012 | Fisker et al. | |
| 2012/0327196 A1* | 12/2012 | Ohba | G06T 11/00 348/49 |
| 2013/0316298 A1* | 11/2013 | Ikegami | A61B 6/032 433/29 |
| 2014/0362091 A1* | 12/2014 | Bouaziz | G06T 15/503 345/473 |
| 2015/0265374 A1* | 9/2015 | Masoud | G06K 9/00208 382/128 |

FOREIGN PATENT DOCUMENTS

| | | |
|---|---|---|
| DE | 102013102421 A1 | 9/2014 |
| WO | 2004098378 A2 | 11/2004 |
| WO | 2010042290 A1 | 4/2010 |
| WO | 20100042990 A1 | 4/2010 |

OTHER PUBLICATIONS

International Search Report; PCT/EP2016/077934; Mar. 9, 2017 (completed); dated Mar. 21, 2017.
Peter Eisert et al.: "Virtual Mirror: Real Time Tracking of Shoes in Augmented Reality Environments".
ETHzurich; "A sweeter smile through Augmented Reality"; 20174-05-09; Claudia Hoffmann.
Written Opinion of the International Searching Authority; PCT/EP2016/077934; Mar. 9, 2017 (completed); dated Mar. 21, 2017.

\* cited by examiner

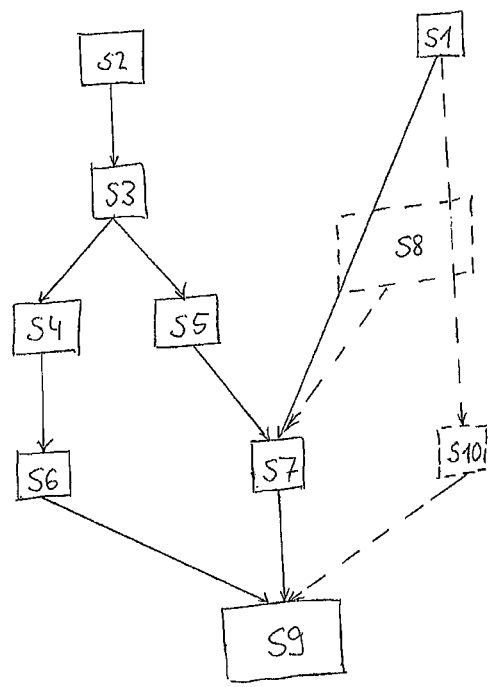
Fig 1
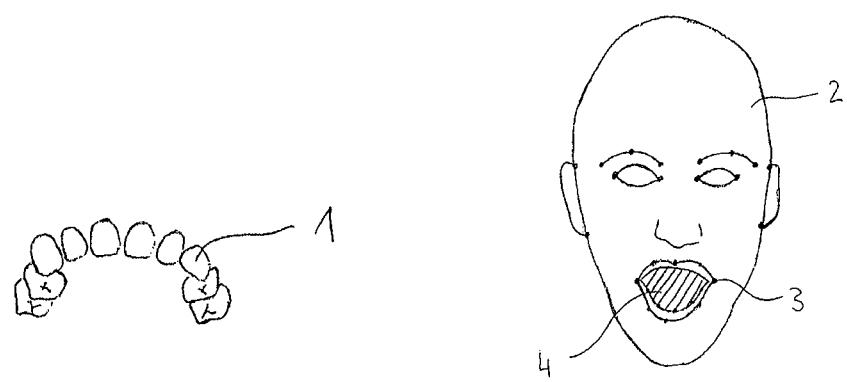
Fig. 2
Fig. 3

METHOD FOR VISUALIZING A TOOTH SITUATION

TECHNICAL FIELD

The invention relates to a method for visualizing a tooth situation, wherein a virtual tooth data record of the tooth situation is available and wherein an image of the face of a patient is recorded and stored as a facial data record.

STATE OF THE ART

Previous methods for visualizing a tooth situation, for example for visualizing the effect of a planned dental prosthesis on the face of a patient, usually show a frozen or at least rotatable image of the face of the patient, into which a virtual tooth situation is incorporated with proper orientation and positioning.

A method for visualizing a tooth situation is known, for example, from DE 20 2008 014 344 U1, DE 10 2013 102 421 A1 or US 2012/0095732 A1.

A variety of methods for automatically recognizing the characteristics of a face, or of feature points of a face, in images of the face are known, for example, from D. Vukadinovic and M. Pantic, "Automatic Facial Feature Point Detection using Gabor Feature Based Boosted Classifiers" (2005) IEEE International Conference on Systems, Man and Cybernetics, from M. Dantone et al, "Real-time Facial Feature Detection using Conditional Regression Forests" (2012) IEEE Conference on Computer Vision and Pattern Recognition or from US 2010/030578 A1.

The object of the present invention is to further develop and improve the prior art.

Presentation of the Invention

The subject matter of the invention is a method for visualizing a tooth situation, wherein an image of the face of a patient is recorded and stored as a facial data record, wherein feature points within the facial data record are automatically recognized by means of a facial recognition method, wherein a mouth area located between the lips is recognized automatically on the basis of the feature points, wherein a position of the face in the facial data record and a three-dimensional direction of an orientation of the face in the facial data record is automatically recognized on the basis of the feature points, wherein the tooth data record is oriented according to the three-dimensional direction of the orientation of the face and positioned according to the position of the face with respect to the facial data record, wherein the mouth area within the facial data record is partially overlaid and/or overlaid and/or replaced by the tooth data record, and the result is displayed as a visualization data record.

It should be noted that the tooth situation can be any tooth situation, involving one tooth or multiple teeth, as well as an image of a complete set of teeth. It can be a purely virtually planned data record, for example, or it can be a data record of a planned dental prosthesis generated from a model by means of a scan. It can also be a data record of the actual tooth situation, generated by means of a camera, for example. The latter can be supplemented with or manipulated around dental prosthesis parts for instance, for example to show the planned result of an orthodontic treatment.

Feature points, often also referred to as facial feature points (FFP) or as biometric feature points, are points that, within the framework of a two-dimensional or three-dimensional facial recognition method, can automatically be recognized in a face, i.e. by means of a computer and without interaction of the user; e.g. the tip of the nose, the corners of the mouth, the eyes, etc.

One advantage of the method according to the invention is that a planned tooth situation can be visualized for a patient or a treating physician or dental technician within the face of the patient. The combination of current data representing reality with virtual data is often referred to as augmented reality. The effect of the planned tooth situation is in particular demonstrated by complete superimposition of the planned tooth situation onto the current tooth situation or replacement of the current tooth situation by the planned tooth situation. A planned tooth situation and a current tooth situation can be displayed simultaneously with a partial superimposition of the planned tooth situation onto the current tooth situation. For example, the planned tooth situation and the current tooth situation, i.e. the range of the facial data record within the mouth area, can be displayed in a different color and transparently. As a result, for example when preparing the current tooth situation, the conformity with or deviation from a planned tooth situation can be verified.

Advantageously, the facial data record is two-dimensional or three-dimensional. A two-dimensional data record is easy to generate, or can be generated by means of a simple device, e.g. a camera, whereas a better quality of the visualization data record can be achieved with a three-dimensional data record.

Advantageously, the tooth data record is three-dimensional. The tooth data record can therefore easily be combined with the facial data record in an orientation adapted to the orientation of the face in the facial data record, or displayed within the visualization data record.

The method is advantageously rerun at timed intervals. A continuous or repeated generation of a visualization data record to an updated, i.e. newly recorded, image of the face produces a type of virtual mirror image of the face. The patient can thus turn or move his head, open his mouth, etc., and is consistently shown an image of his face adapted to the current orientation or current expression on his face, and with the planned tooth situation properly overlaid. The reruns can be performed automatically, for example; e.g. at consistently equal time intervals. A trigger mechanism to initiate the reruns could also be provided, however. This could possibly lead to different time intervals.

The time intervals are advantageously no more than 42 ms, as a result of which a frame rate of 24 Hz, typical for videos, is achieved, and with it a visualization in real time. In order to ensure correct recognition, at least four feature points are advantageously automatically identified for the automatic recognition of the mouth area.

At least one three-dimensional additional data record is advantageously oriented according to the three-dimensional direction of the orientation of the face and positioned according to the position of the face with respect to the visualization data record, wherein the facial data record and/or the tooth data record in the visualization data record is partially overlaid and/or overlaid and/or replaced by the additional data record. In this way, additional information can easily be displayed within the visualization data record and presented clearly to a user.

The additional data record is advantageously an image of a tooth root, segmented from a volume data record and correlated to a current tooth situation with respect to the position, an image of a nerve in the jaw, segmented from a magnetic resonance tomography image and correlated to a current tooth situation with respect to the position, an image of a mandibular joint or an image of a drill or a drill hole. For the purpose of planning or monitoring, a planned course of a drill hole, for example, or a current position of a drill determined by means of a sensor, can be displayed in the visualization data record.

BRIEF DESCRIPTION OF THE DRAWINGS

Design examples of the invention are outlined in the drawings. The drawings show:

FIG. 1 a schematic image of a first embodiment of a method according to the invention, FIG. 2 a schematic view of a digital data record of a dental prosthesis designed for the treatment of a patient, FIG. 3 a schematic view of a two-dimensional digital data record of the face of a patient, FIG. 4A, B a schematic view of a facial data record with feature points for determining the orientation of the face within the facial data record and FIG. 5 a schematic view of a visualization of a planned dental prosthesis.

DESIGN EXAMPLES

Figures 4A, 4B:
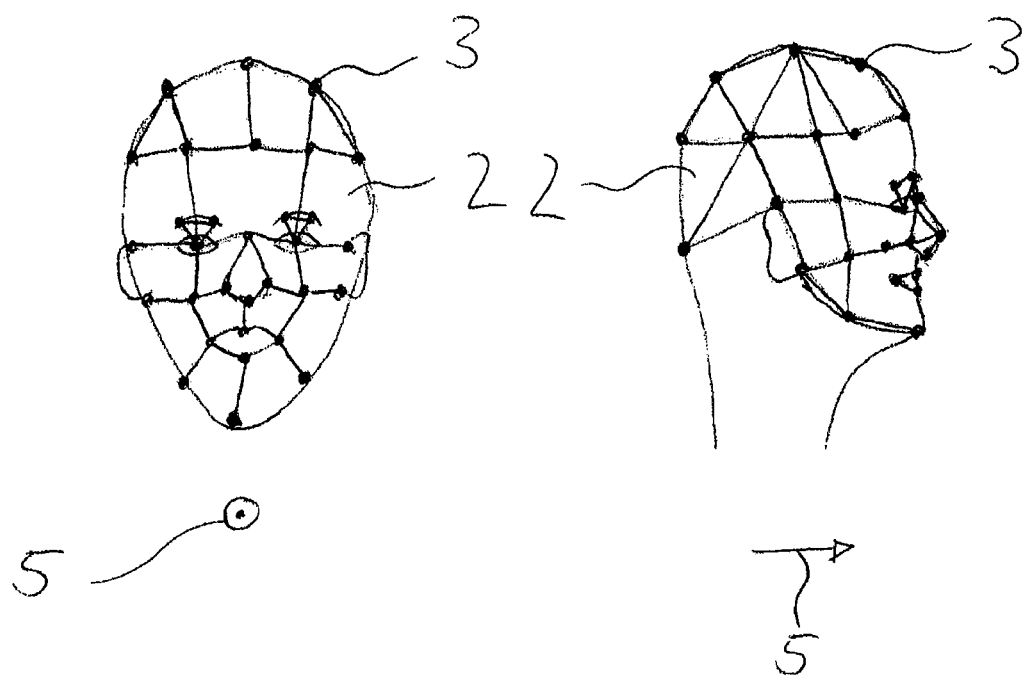

A first embodiment of a method according to the invention is outlined in FIG. 1.

A three-dimensional tooth data record 1 of a dental prosthesis designed for a patient is provided according to a method step S1. An example of a three-dimensional tooth data record 1 is outlined in FIG. 2.

In order to show the result to be achieved with the dental prosthesis to a patient, according to a method step S2, one facial data record 2 is provided by recording a two-dimensional image of the face of the patient, or a series of facial data records 2 is provided by recording a series of two-dimensional images at short time intervals, wherein one respective facial data record 2 is generated for each image of the series. The one or more two-dimensional images can be recorded by using a camera, for example. The face can be filmed, e.g. with a camera. An example of a facial data record 3 is shown in FIG. 3.

With the aid of a facial recognition method, feature points 3, i.e. characteristic points of the face, such as the corners of the mouth, are identified within the facial data record 2 in a method step S3. In a method step S4, the mouth or the lips are identified in the facial data record 2 on the basis of the recognized feature points 3.

As shown in FIGS. 4A and 4B with two differently oriented faces, a three-dimensional direction 5 of the orientation of the face of the patient in the facial data record 2 is determined on the basis of the feature points 3 in a method step S5. While the direction 5 of the orientation of a front-facing orientation of the face extends perpendicular to the image plane of the facial data record 2 and out of the image plane, for example, the direction 5 for a face recorded in profile lies within the image plane. In method step S5, the three-dimensional orientation of the face is thus deduced from the two-dimensional image of the face.

Figure 5:
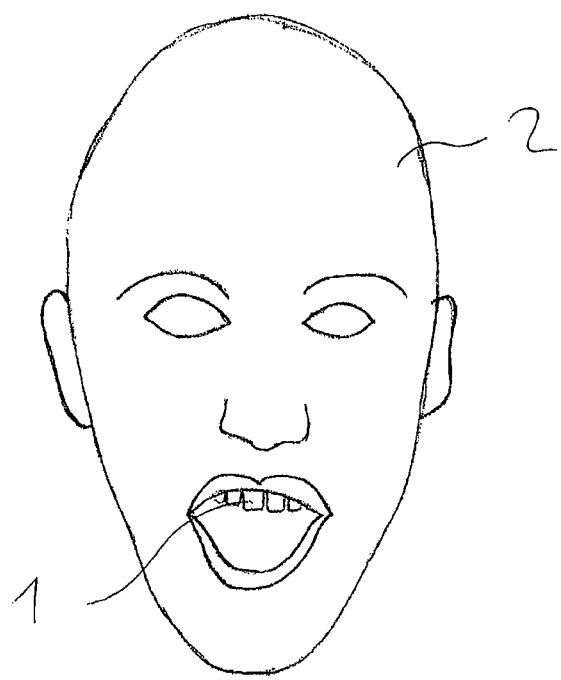

As outlined in FIG. 5, in a method step S6 following method step S4, an area located between the lips is segmented and cut out as a mouth area 4 within the facial data record 2.

In a method step S7, the tooth data record 1 is rotated and positioned relative to the image plane of the facial data record 2 in such a way that the orientation of the tooth data record 1 matches the determined direction 5 of the orientation of the face and the position matches the position of the mouth area 4.

To do this, the relative orientation of the dental prosthesis to the face is established in method step S8, for example on the basis of a relationship of an orientation of the tooth data record 1 within the image plane to a direction of the orientation of the face within the facial data record 2. The relationship to the orientation of the face in the facial data record 2 can, for instance, be established on the basis of existing teeth that will remain or teeth that are to be replaced. The relevant data is stored, so that the orientation of the tooth data record 1 takes place automatically in method step S7 with the aid of the stored data and the determined orientation 5 of the face within the facial data record 2. Method step S8 therefore does not have to be rerun for every generated facial data record, and for this reason is indicated with dashed lines in FIG. 1.

It is also possible to perform the orientation according to method step S8 once by hand. The thus produced relative orientation of the tooth data record 1 to the direction 5 of the orientation of the face within the facial data record 2 is subsequently stored so that then, in the event of a change in the orientation of the face and a resulting change in the direction 5, the tooth data record can be positioned automatically.

In a method step S9, the oriented three-dimensional tooth data record 1 is displayed behind the facial data record. The data record consisting of the facial data record 2 and the tooth data record 1 with the cut-out mouth area 4 and shown schematically in FIG. 5 is referred to here as the visualization data record.

According to a further development, the tooth data record 2 is edited in a method step S10 prior to merging and displaying the facial data record 2 and the tooth data record 1. The provided tooth data record 2 is typically a data record generated for a CAM method using a CAD method, i.e. a data record that is generated for a computer-aided manufacturing method. A data record intended for use in computer-aided manufacturing merely has to include information pertaining to the shape, i.e. the position of the surface. For the method according to the invention, however, it is advantageous for the appearance of the tooth data record 1 to be as realistic as possible. For this purpose, the tooth data record 1 provided according to method step S1 is edited according to the optional method step S10.

If the facial data record is repeatedly provided at regular time intervals according to method step S2 and at least method steps S3, S4, S5, S6, S7 and S9 are respectively carried out for each new facial data record, the display means is the equivalent of a virtual mirror or the continuously regenerated visualization data record is the equivalent of a virtual mirror image. The patient can move his head and/or open and close his mouth, and see the effect of the planned dental prosthesis from a variety of perspectives. In particular when a recording means for generating the images of the face of the patient is arranged at the smallest possible distance from the display means, the effect of a mirror image, displaying the face of the patient in a current orientation and augmented with the planned dental prosthesis, is achieved.

If the mouth area 4 of the facial data record 2 is not cut out in method step S6, but is instead only identified and partially overlaid with the tooth data record 1, a deviation of a current tooth situation from a planned tooth situation can be visualized. To do this, the mouth area 4 and the tooth data record 1, for example, are displayed simultaneously and in a partially transparent manner; for instance with different colors. This visualization permits easy monitoring of a preparation in real time, or real-time monitoring of the current tooth situation when carrying out a preparation of the tooth situation.

It is also possible to incorporate an additional data record into the visualization data record by orienting the additional data record according to the determined direction 5 of the orientation of the face and the position of the face in the facial data record 2 and superimposing said additional data record on the facial data record 2 and/or the tooth data record 1.

Additional information, e.g. regarding the nerve in the jaw, the mandibular joint, tooth roots, the location of a planned drill hole or the position and orientation of a current drill during use, can be displayed clearly.

LIST OF REFERENCE SIGNS

1 Tooth data record
2 Facial data record
3 Feature points
4 Mouth area
5 Direction of an orientation of a face within the facial data record
S1-S9 Method steps

The invention claimed is:

1. A method for visualizing a tooth situation comprising: generating a visualization data record by:
 a) recording an image of a face of a patient and storing said image as a facial data record;
 b) automatically recognizing feature points within the facial data record using a facial recognition method,
 c) automatically recognizing a mouth area located between the lips on the basis of the feature points,
 d) automatically recognizing a position of the face in the facial data record and a three-dimensional direction of an orientation of the face in the facial data record on the basis of the feature points,
 e) orienting a virtual tooth data record of the tooth situation according to the three-dimensional direction of the orientation of the face and positioning said virtual tooth data record according to the position of the face with respect to the facial data record,
 f) partially overlaying, overlaying or replacing the mouth area within the facial data record by the virtual tooth data record, and
 g) displaying the result as the visualization data record and responsive to obtaining the visualization data record for the image of the face of the patient, and at defined time intervals, repeating steps a)-g) using a new image of the face of the patient recorded at the defined time intervals to produce a new corresponding visualization data record such that a continuous real-time generation and display of new corresponding visualization data records each corresponding to one new image, is produced in order to provide a virtual mirror image for said face; wherein in each new image the orientation or expression of the face of the patient has changed.

2. The method according to claim 1, wherein the facial data record is two-dimensional or three-dimensional.

3. The method according to claim 1, wherein the virtual tooth data record is three-dimensional.

4. The method according to claim 1, wherein the defined time intervals are no more than 42 ms.

5. The method according to claim 1, wherein at least four feature points are automatically identified for the automatic recognition of the mouth area.

6. The method according to claim 1, wherein at least one three-dimensional additional data record is oriented according to the three-dimensional direction of the orientation of the face and positioned according to the position of the face with respect to the visualization data record, and that the facial data record or the virtual tooth data record in the visualization data record is partially overlaid or overlaid or replaced by the additional data record.

7. The method according to claim 6, wherein the additional data record is an image of a tooth root which is segmented from a volume data record and correlated to a current tooth situation with respect to the position.

8. The method according to claim 6, wherein the additional data record is an image of a nerve in the jaw which is segmented from a magnetic resonance tomography image and correlated to a current tooth situation with respect to the position.

9. The method according to claim 6, wherein the additional data record is an image of a mandibular joint.

10. The method according to claim 6, wherein the additional data record is an image of a drill or a drill hole.

11. The method according to claim 1, wherein the virtual tooth data record is edited before partially overlaying, overlaying or replacing the mouth area with said virtual tooth data record.

12. The method according to claim 1, wherein the displaying further comprises displaying a deviation of the virtual tooth data record from a planned virtual tooth data record responsive to the partially overlaying of the mouth area within the facial data record by the virtual tooth data record.

* * * * *